United States Patent
Schlatterer

(10) Patent No.: US 9,387,024 B2
(45) Date of Patent: Jul. 12, 2016

(54) MINIMAL CONTACT CIRCUMFERENTIAL CABLE/WIRE SYSTEM

(71) Applicant: Daniel Robert Schlatterer, Dunwoody, GA (US)

(72) Inventor: Daniel Robert Schlatterer, Dunwoody, GA (US)

(*) Notice: Subject to any disclaimer, the term of this patent is extended or adjusted under 35 U.S.C. 154(b) by 182 days.

(21) Appl. No.: 14/146,214

(22) Filed: Jan. 2, 2014

(65) Prior Publication Data

US 2015/0182269 A1    Jul. 2, 2015

(51) Int. Cl.
*A61B 17/88* (2006.01)
*A61B 17/84* (2006.01)
*A61B 17/82* (2006.01)

(52) U.S. Cl.
CPC ............... *A61B 17/842* (2013.01); *A61B 17/82* (2013.01)

(58) Field of Classification Search
CPC combination set(s) only.
See application file for complete search history.

(56) References Cited

U.S. PATENT DOCUMENTS

| 5,611,801 | A | 3/1997 | Songer |
| 6,589,246 | B1 | 7/2003 | Hack et al. |
| 2005/0171547 | A1* | 8/2005 | Aram ............... A61B 17/82 606/74 |
| 2012/0272816 | A1 | 11/2012 | Ueda et al. |

FOREIGN PATENT DOCUMENTS

JP    2011110365    6/2011

* cited by examiner

*Primary Examiner* — Sameh Boles
(74) *Attorney, Agent, or Firm* — David L. King

(57) ABSTRACT

An improved bone fracture binding has a length of binding having interrupted and discontinuous points of contact. The binding when placed under tension leaving gaps for soft tissue between the bone and the points of contact in the binding while securing and immobilizing the bone fracture. The binding may have a tension cable or wire positioned around the bone spaced above the bone by beads. The beads are closely spaced about the cable or wire to space the wire a distance above the bone. The beads are preferably abutting and spaces between the adjacent beads form the gaps for soft tissue. The beads are round, and preferably shaped as ovals or spheres. The cable or wire in the binding maintains tension force when tensioned around the bone.

8 Claims, 5 Drawing Sheets

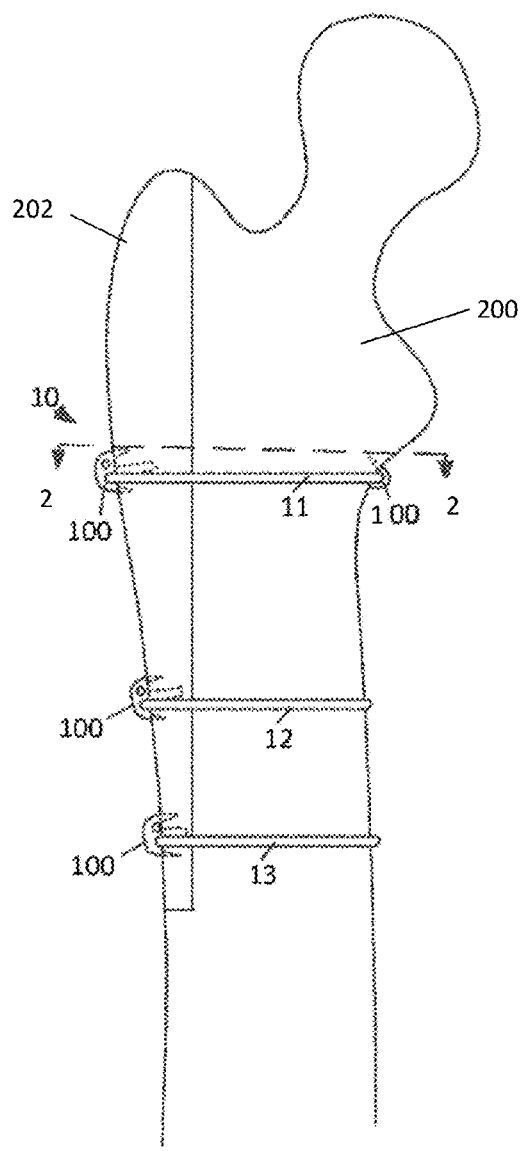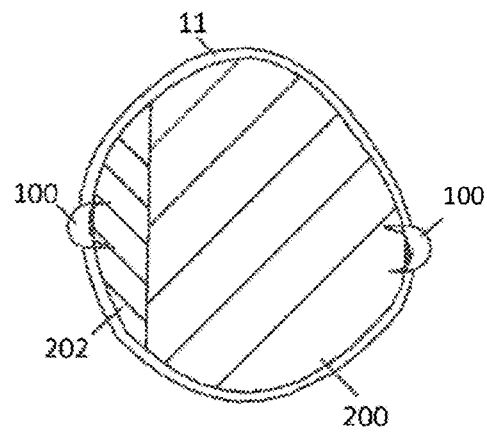
FIG. 1
PRIOR ART
FIG. 2
PRIOR ART

MINIMAL CONTACT CIRCUMFERENTIAL CABLE/WIRE SYSTEM

TECHNICAL FIELD

The present invention relates to an improved binding for securing and immobilizing bone fractures, osteotomies, or other instances of bony instability. This invention also relates to securing hardware, metal plates, for example, to bone. One such application would be for fractures or orthopedic adult reconstructive procedures, revision hip or knee procedures and so forth.

BACKGROUND OF THE INVENTION

Often bone fractures are immobilized and the bones are tensioned by a wire or cord bringing the break closed so the healing of the fracture can occur by new bone growth. Typically, a wire or metal cord or cable is used as a binding. These bindings are generally wound around the break and tensioned and crimped to hold the break in close contact to allow the break to fuse with new bone growth. Ideally, fractures fuse in three months or less. In some cases up to one year. It is therefore essential the binding stays under tension for at least the typical three months, if not for at least a year.

The metals of the wire or cord are typically stainless steel or other alloy that does not corrode in the body. Attempts to use flat braided nylon bindings is disclosed in US 2012/0272816 A1 to allow accommodations of soft tissue attachment to bound bone fractures. In this disclosure it points out braid loses a significant amount of its tensile strength and under relaxation when gaps in the braid expand in contact with living tissues.

In bone surgeries, such as for fixation (i.e., fusion and unification of bones) of repositioned bones after bone fracture, e.g., fracture of the spine, bone grafting, and the like, the bones, in order for their fixation, must be kept tightly held together, so that they may not be dislocated before their fusion is completed. For this holding, steel wires have long been used, along with, depending on situations, a variety of devices such as metal, plates, rods, hooks, bolts (pedicle screws) and the like. However, flat cables formed by braiding ultra-high molecular weight polyethylene fibers (molecular weight: not less than 400000), a type of polyethylene fibers, namely high strength fibers having high tensile strength and high tensile modulus of elasticity, have recently come to be widely used for tying bones, in place of steal wires, taking advantage of their high strength and flexibility. Flat cables are used for soft tissues, such as ligaments.

However, it has been found that ultra-high molecular weight polyethylene fiber is a material that degrades. Braiding fine fibers of ultra-high molecular weight polyethylene revealed that degradation and accompanying decline in strength are more likely to proceed if the flat cables contact with living tissues on the flat cables' surface which is widened due to expansion of their inter-fiber gaps.

Conventional flat cables formed by braiding ultra-high molecular weight polyethylene fibers shrink in their cross section area when a tensile force is applied to them, because the fibers are pulled to come into close together and their degree of congestion is increased, whereas in a relaxed state when they are released from the tensile force, their cross section expands because of expansion of the gaps between the fibers and decrease in the degree of their congestion. It was confirmed increased contact of individual fibers with the living tissues, degradation of the fibers become faster when the cross section area of flat cables is expanded than when the cross section area of the flat cables is shrunk. Flat cables made of ultra-high molecular weight polyethylene fibers, when tied to bones in the body, are usually under a tensile force, but as the levels of the tensile force vary depending on the posture and motion of the body, there are also some occasions at which some part of the cable turns into a relaxed state. When relaxed and a cross section of the flat cables expands, with the gaps between the fibers expanding, the fibers come into wider contact with living tissues, thereby becoming more susceptible to degradation. This is still more important where the flat cables are applied to soft tissues, for which strong fastening is avoided. Therefore, it is desirable that surgical flat cables to be used in tying bones or suturing soft tissues like ligaments is those whose cross section area expands only a little even in a relaxed state. However, it was practically very difficult to produce such flat cables by braiding fibers.

So braided cables, while accommodating soft tissue, is clearly less than an ideal solution. Smooth steel or metal wire tensioned and crimped around the bone fracture strangulates the periosteal blood vessels surrounding the bone killing the tissue around the entire 360 degree circumference of the bone.

It is therefore an objective of the present invention to provide a bone binding construct capable of securing the bone fracture while avoiding or greatly minimizing damage to the underlying blood vessels on/in the periosteal tissue. These and other objectives are achieved by the invention as described below.

SUMMARY OF THE INVENTION

An improved bone binding has a length of binding having interrupted and discontinuous points of contact. The binding when placed under tension leaving gaps for soft tissue between the bone and the points of contact in the binding while securing and immobilizing the bone fracture. The binding may have a tension cable or wire positioned around the bone spaced above the bone by beads. The beads are sufficiently closely spaced about the cable or wire to space the wire a distance above the bone. The beads preferably are fixed spatially about the wire or even abutting with spaces between the adjacent beads forming the gaps for soft tissue. The beads are round, and preferably shaped as ovals or spheres. The cable or wire in the binding maintains tension force when tensioned around the bone. The circumferential distance of the wire encircles the bone diameter at a diameter greater than the bone due to the use of the beads.

The invention provides a method of immobilizing a bone fracture or osteotomy or hardware for reconstructive purposes and so forth having the steps of isolating the region of the bone to be immobilized, binding the bone with a length of binding having interrupted discontinuous points of contact, tensioning the binding leaving gaps for the soft tissue to occupy between the bone and the points of contact in the binding while securing and immobilizing the bone and clamping the binding and immobilizing the bone.

BRIEF DESCRIPTION OF THE DRAWINGS

The invention will be described by way of example and with reference to the accompanying drawings in which:

FIG. 1 is a side view of a prior art bone fixation system showing an allograft fixed to a femur.

FIG. 2 is a cross sectional view taken along lines 2-2 of prior art FIG. 1.

DETAILED DESCRIPTION OF THE INVENTION

Figure 3A:
FIGS. 3A-3D are a prior art hip repair.
Figure 3B:
Figure 3C:
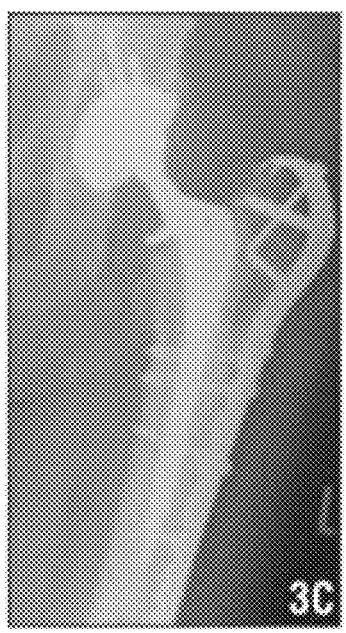
Figure 3D:

With reference to prior art FIGS. 1 and 2, an exemplary cable fixation system is shown. The prior art cable system 10 can be used in circumferential configurations. In the illustrated embodiment, the cable system 10 can include three wires, cords or cables 11, 12, 13 made of metal or any other material that are circumferentially tensioned around a femur bone 200 to secure a structural allograft 202 to the femur bone 200. In this embodiment, a portion of the femur bone 200 can be cut away and the structural allograft 202 can be cut match the cut away portion of the femur bone 200. The structural allograft 202 is then placed against the femur bone 200 at the cut away section and held in place by the cable system 10. The structural allograft 202 must be held in compression against the bone 200 for the injury to heal properly. Each of the cables 11, 12, 13 must be held in tension around the circumference of the bone 200. Typically, the tensioning force is 130 foot pounds, depending upon the density, strength and other biochemical properties of any one particular bone the tensioning force may need to be greater or lesser than 130 foot pounds. This tension causes no problem around the allograft 202, but crushes the periosteal vessels on the living bone tissue of the femur bone 200. The cables 11, 12, 13 are coupled to cable anchor crimps 100. The cable anchor crimps 100 are rigidly attached to the structural allograft 202 with tacks and/or bone screws. Cable stops are attached to one end of the cables and the cable anchor crimps 100 can be rigidly attached to the cable stops. The cables 11, 12, 13 are wrapped around the femur bone 200 and the structural allografts 202 and tensioned to a required force. The opposite end of the cables 11, 12, 13 are crimped to the cable anchor crimps 100 and the excess cable 11, 12, 13 are cut away. It is critical that the cables 11, 12, 13 not move across the bone. In this illustrative example the structural allograft 202 could be substituted with a plate with the intent of stabilizing the femur bone 200. The structural allograft 202 as illustrated could also represent a femoral osteotomy subsequently stabilized and bound back to the femur with wires, cords or cables.

With reference to FIGS. 3A-3D, photos of a hip procedure using a prior art cable system is shown. This exemplary prior art technique is representative of a use of conventional metal cords used in bone repair fixation. In the case of a typical bone fracture, the same cords and anchors are used to encircle the bone to close the fracture and immobilize the break. As can easily be appreciated, this crushes any underlying periosteal vessels and cuts through any soft tissue between the bone and the cord. This has been an accepted consequence of the desire to completely ensure the bones are held fixed in place.

Figure 4:
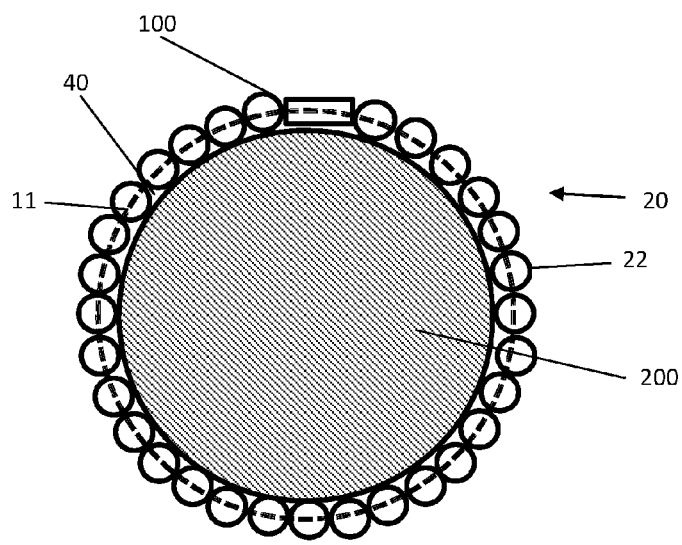
FIG. 4 is an exemplary cross sectional view of a femur bone similar to FIG. 2, but with a bone fracture binding made in a first embodiment in accordance with the present invention.

With reference to FIG. 4, an exemplary cross sectional view of a femur bone similar to that shown in the prior art FIG. 2 has a bone binding 20 made in accordance to the present invention. The binding 20 has the cord 11 passing through a plurality of spherical beads 22. As shown, the beads 22 are abuttingly arranged tightly around the cord 11 in such a fashion that they reposition the cord 11 from direct contact with the bone 200 outwardly by a distance of approximately one half the diameter of the spherical shape of bead 22. The distance between adjacent beads 22 creates a gap 40 through with soft tissue and other vascular material can extend without being strangulated by the crush of a tightened and tensioned cord 11. As shown, the cord 11 is raised above the bone structure 200 on each side by the distance of one half the diameter or the radius of the bead 22. The beads 22 being of a spherical shape provide a very limited contact area into the hardened surface of the bone. These contact areas are the only points of contact around the bone surface that could inhibit any soft tissue growth. As a result, this binding when put under tension provides a superior way in which to minimize the trauma or injury to any soft tissue or periosteal blood vessels underlying the cord. As a result, this binding when put under tension provides a minimal contact circumferential cable/wire system.

Figure 4A:
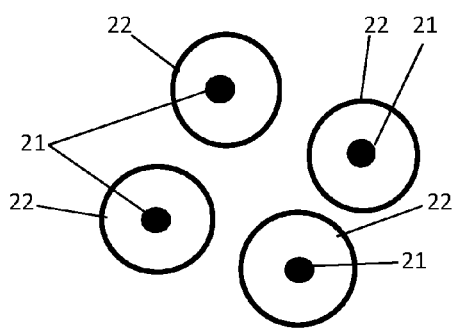
FIG. 4A shows a plurality of exemplary beads of a spherical shape for use in the present invention.

FIG. 4A shows a plurality of the exemplary beads 22 having an opening 21 through which the cord 11 can pass.

Figure 4B:
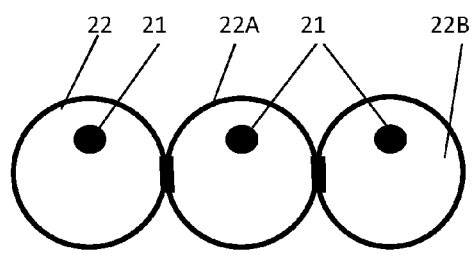
FIG. 4B shows an exemplary bead structure having a row of three beads affixed together to provide a wide binding wherein three cords can be passed to form the wide binding.

With reference to FIG. 4B, the exemplary bead structure is made into a row of three beads 22, 22A, 22B that are affixed together in such a fashion to provide a wide bone fracture binding 20. This wide bone binding 20 can be utilized by passing three cords 11 through the openings 21 in each of the adjacent beads 22, 22A, 22B. When this is done, a typical bone anchor 100 or three bone anchors 100 can be applied around the ends of the cords 11 encircling beads 22, 22A, 22B such that a plurality of the aligned rows of beads 22, 22A, 22B can stably provide contact points around the circumference of the bone 200 not only in the circumferential direction, but also down the longitudinal length of the bone 200. This is particularly useful when soft tissue or ligaments are going to be adhered to the bone 200 and there is a need to provide a wider contact area in order to safely and with minimum trauma hold the bones in place along with the soft tissue or ligament that is to be attached to the bone 200.

Figure 5:
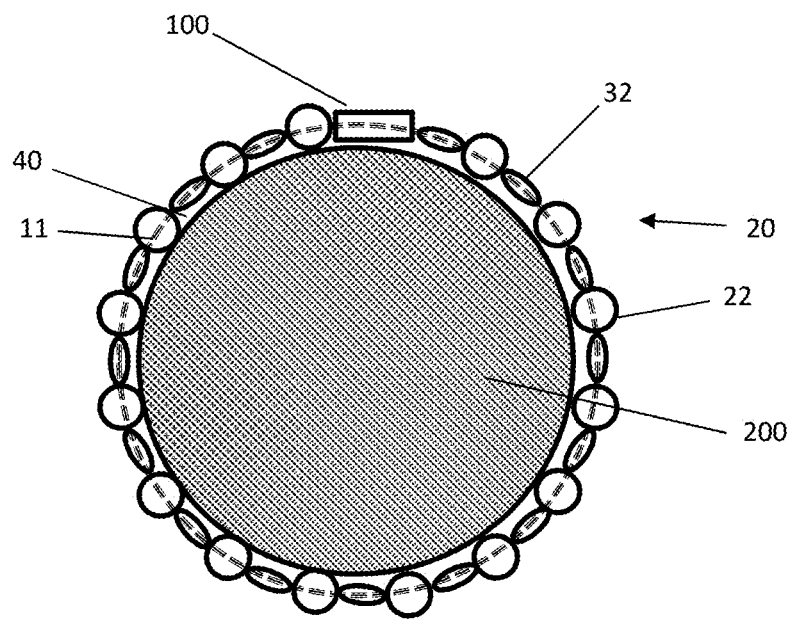
FIG. 5 is an alternative construction of the present invention.

With reference to FIG. 5, an alternative construction of the present invention is shown wherein a plurality of small beads 22 with the small beads 22 being spaced by spacers 32 on the cord 11. The small beads 22 being in direct contact with the bone 200 and the spacers 32 are smaller and spaced above so the bone 200 that it provides even more gap space 40 for the tissue.

It is believed important that the beads 22 be either fixed to the cord 11 so that they cannot move relative to the length of the cord 11 when the bone cord is placed in tissue when used as a binding or alternatively that there are a sufficient number of beads 22 or beads 22 and spacers 32 that they are in an abutting relationship. If the beads 22 cannot be configured in an abutting relationship, then the beads in combination with spacers 32 as shown can be utilized in such a fashion that the beads 22 cannot move longitudinally down the length of the cord 11. It is important that the beads 22 be fixed in a location and prevented from movement either along the cords length or also prevented from movement that could cause the beads 22 to roll and leave their secure position affixing the binding to the bone fracture. Alternatively, a random number of unsecured beads could be spaced randomly and the subsequent tensioning of the cable/wire system would suffice for binding the bone, fracture, osteotomy, plate and so forth.

Figure 6:
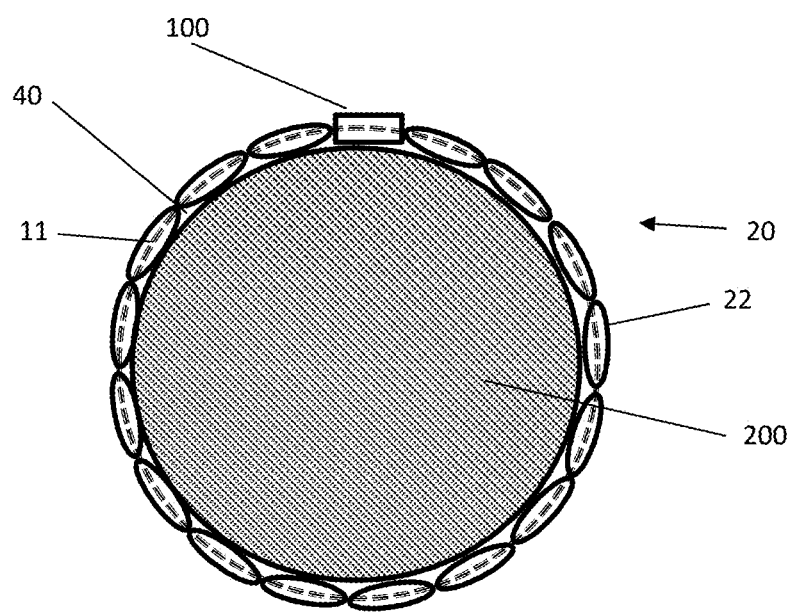
FIG. 6 is a third embodiment of the present invention.
Figure 7:
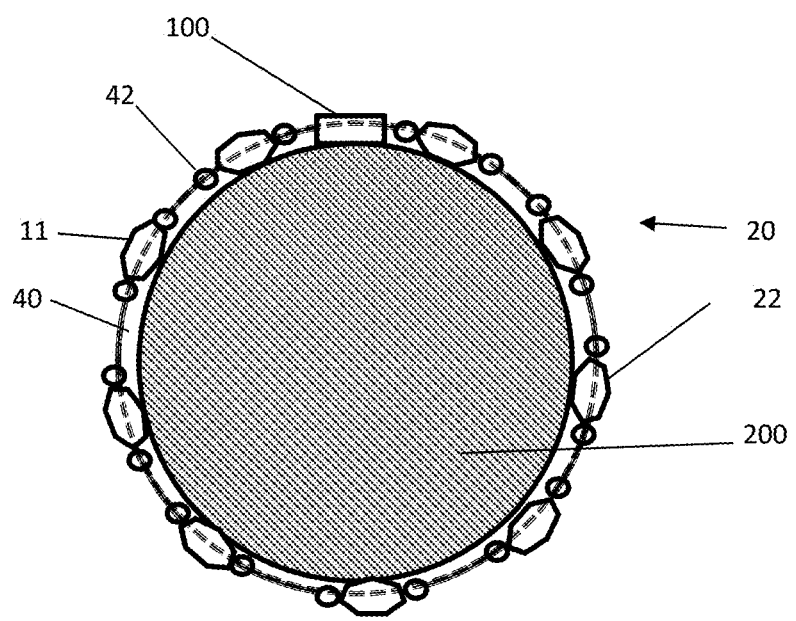
FIG. 7 is a fourth alternative embodiment of the present invention.

With reference to FIG. 6, a third embodiment of the present invention is shown In the alternative construction, there are a plurality of oval shaped beads 22 wherein the beads 22 are in an abutting relationship and the bead is provided in an oblong oval shape further increasing the gap 40. As a result, the beads 22 can be any number of combinations of shapes as shown in FIG. 7, an exemplary view of a combination of bead shapes 22, 42 is provided. In this embodiment, the small beads 42, as illustrated, can be crimped onto the cord 11 on each end of the bead 22 to prevent movement along the cord 11. This embodiment greatly reduces the contact points to the bone 200 and beads 22. As shown, the beads 22 have flats that locally increase bone contact, but reduce rolling or movement.

Figure 8:
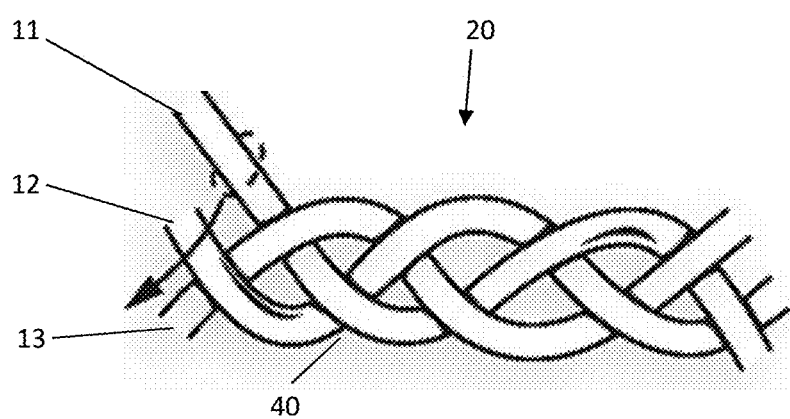
FIG. 8 is a fifth alternative embodiment of the present invention.

FIG. 8 shows a fifth embodiment bone binding 20 of a braided wire construction showing two or more, preferably three, large diameter wires or cords 11, 12, 13 of 2.0 mm or greater diameter braided around each other wherein the braid can be stretched taut and leaving gaps 40 for the soft tissue to reside without being crushed. This braided wire or cord avoids the use of conventional fine wires that are closely packed to be virtually smooth along the length, but is made to achieve deliberately interrupted and discontinuous points of contact when tensioned to insure large numerous voids or gaps 40 to protect the soft tissue.

The improved bone binding 20 is superior to conventional cords or cabling for providing bone stability in any and all situations of bony instability. All situations of fracture, osteotomy, non-union and need or use for binding of said bone including but not limited to the inclusion of metal plates or other hardware devices to achieve bone stabilization. In some situations the use of a metal plate secured to bone with this cabling concept would be prophylactic in purpose; meaning, securing a plate with cables to add stability to a non-fractured bone and to reinforce the bone and prevent future complications including fracture. The improved bone binding makes reference to any and all materials for circumferential wiring or cabling protocols to impart bone binding, plate binding, and other indications for circumferential wiring or cabling protocols. This includes use of a single wire, a single cable, a braided wire or braided cable or any variation in material and/or variation in physical configuration thereof. The present invention bone binding collectively conveys an intent to spare the soft tissues adjacent to bone the ischemia and damage currently imparted by flat wiring/cable systems by the use of this minimal contact circumferential cable/wire systems unique bone binding.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

I claim:

1. An improved bone binding comprises:
a length of binding having interrupted and discontinuous points of contact when placed under tension leaving gaps for soft tissue between the bone and the points of contact in the binding while securing and immobilizing the bone, wherein the binding has a tension cable or wire positioned around the bone spaced above the bone by beads, the beads having an opening through which the cable or wire can pass and the beads being closely and abuttingly arranged, each bead abutting an adjacent bead so the beads are prevented from moving along the length of the binding cable when tightened around the bone and to prevent the beads from rolling at the points of contact should the cable or wire impart a twist.

2. The improved bone binding of claim 1 wherein the beads are round.

3. The improved bone binding of claim 2 wherein the beads are ovals or spheres.

4. The improved bone binding of claim 1 wherein the cable or wire in the binding maintains tension force when tensioned around the bone.

5. The improved bone binding of claim 1 wherein the cable or wire can be made from any and all materials for circumferential wiring or cabling protocols to impart bone binding, plate binding, and other indications for circumferential wiring or cabling protocols, this includes use of a single wire, a single cable, a braided wire or braided cable or any variation in material and/or variation in physical configuration thereof.

6. The improved bone binding of claim 1 wherein the bone binding is a braided wire or cord construction having two or more large diameter wires or cords braided together to create numerous voids or gaps to protect soft tissue or vessels between the bone and the bone binding.

7. The improved bone binding of claim 6 wherein the braid has three wires or cords.

8. The improved bone binding of claim 7 wherein the wire or cord diameter is 2.0 mm or greater.

\* \* \* \* \*